United States Patent [19]
Studt et al.

[11] Patent Number: 4,564,640
[45] Date of Patent: Jan. 14, 1986

[54] AMIDINOUREAS SUBSTITUTED IN BOTH THE UREA AND AMIDINO NITROGEN POSITIONS

[75] Inventors: William L. Studt, Harleysville; Richard L. Riley, Chalfont; George H. Douglas, Malvern, all of Pa.

[73] Assignee: William H. Rorer, Inc., Fort Washington, Pa.

[21] Appl. No.: 576,414

[22] Filed: Feb. 2, 1984

Related U.S. Application Data

[63] Continuation-in-part of Ser. No. 280,787, Jul. 6, 1981, abandoned.

[51] Int. Cl.⁴ .............................................. A61K 31/17
[52] U.S. Cl. ..................................... 514/598; 514/597; 564/49; 564/50; 564/52; 564/53; 564/48
[58] Field of Search ................ 424/322; 514/596, 597, 514/598

[56] References Cited

PUBLICATIONS

Douglas, Arzneimittel Forschung-Drug Res. 28(11) 1433, (1978).

Primary Examiner—Robert Gerstl
Attorney, Agent, or Firm—James A. Nicholson; Alexis Barron; Martin F. Savitzky

[57] ABSTRACT

A method of inducing blood pressure reduction in humans and mammals by administering 2,6-disubstituted phenyl N-alkyl amidinoureas in which the phenyl ring is additionally substituted by a hydroxy, alkoxy, aralkoxy, alkenyloxy, alkynyloxy, acyloxy or halo acyloxy group and a novel class of amidinourea compounds having pharmaceutical uses, including blood pressure lowering activity.

4 Claims, No Drawings

AMIDINOUREAS SUBSTITUTED IN BOTH THE UREA AND AMIDINO NITROGEN POSITIONS

FIELD OF THE INVENTION

This invention relates to certain substituted phenyl N-alkyl amidinourea compounds which exhibit blood pressure lowering activity as well as other pharmaceutical properties.

REPORTED DEVELOPMENTS

Amidines and related compounds are known to exhibit anti-hypertensive properties as centrally acting antihypertensive agents.

Certain amidinoureas have been described as possessing blood pressure lowering effects in recently-issued patents, such as U.S. Pat. No. 4,088,785 which discloses that amidinoureas in which an amidino nitrogen is phenyl substituted exhibit blood pressure lowering effects in tests using the spontaneous hypertensive rat. (Tabei et al, Clin, Pharm. and Therap. 11: 269–274, 1970) Additionally, U.S. Pat. No. 4,117,165 discloses blood pressure lowering activity for amidinoureas in which a urea nitrogen is substituted with a 2,6-disubstituted phenyl group and the amidino nitrogens are unsubstituted.

Amidinourea compounds are also disclosed, and their properties described, in a monograph appearing in Arzneimittel Forschung 28 (II), 1433–1480 (1978). At page 1463 of this monogram, it is disclosed that 1-(2'6'dimethylphenyl)-3-methylamidinourea (also known as lidamidine) has little or no effect on blood pressure over a dose range of 0.1 to 1.0 mg/kg administered intravenously. Later investigations, as reported in U.S. Pat. No. 4,279,928, and assigned to the assignee of the present application, found that this compound has a dose related effect on blood pressure in humans following its oral administration in multiple daily doses.

The present invention relates to certain 2,6-disubstituted phenyl N-alkyl amidinoureas which possess surprising blood pressure lowering effects in humans and animals, including, for example, a blood pressure lowering effect which may be induced relatively quickly after oral administration.

SUMMARY OF THE INVENTION

This invention relates to a method of lowering blood pressure in mammalian species, including humans, which comprises administering to a patient an effective blood pressure lowering amount of a compound according to Formula I

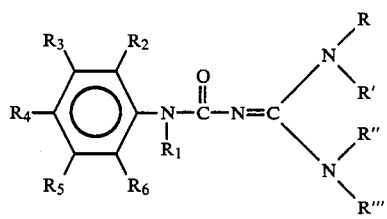

where:
R, R', R", R''' and $R_1$ may be the same or different and are hydrogen or alkyl, provided that at least one of R, R', R", and R''' is other than hydrogen;
$R_2$ and $R_6$ may be the same or different and are alkyl, halo, alkoxy, halo alkyl, nitro or alkylsulfonyl;
$R_3$, $R_4$ and $R_5$ may be the same or different and are hydrogen, hydroxy, alkoxy, aralkoxy, aryloxy, alkynyloxy, alkenyloxy, haloacyloxy, or acyloxy; or
$R_3$ and $R_4$ together are carbonyldioxy, methylenedioxy or ethylenedioxy and form a 5 or 6 membered heterocyclic ring fused to the phenyl ring; provided that at least one of $R_3$, $R_4$ and $R_5$ is other than hydrogen and that $R_3$, $R_4$ and $R_5$ are not all hydroxy;
and the nontoxic pharmaceutically acceptable salts thereof.

Certain compounds of the above formula which fall within the scope of this method are known, but their blood pressure lowering activity has not been recognized (see, for example, U.S. Pat. No. 4,147,804).

This invention also relates to a novel class of compounds possessing pharmaceutical activity, including blood pressure lowering activity, described according to Formula II

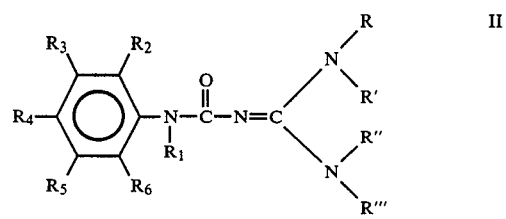

where:
R, R', R", R''' and $R_1$ may be the same or different and are hydrogen or alkyl, provided that at least one of R, R', R" and R''' is other than hydrogen;
$R_2$ and $R_6$ may be the same or different and are alkyl, halo, alkoxy, halo alkyl, nitro or alkyl sulfonyl;
$R_3$, $R_4$ and $R_5$ may be the same or different and are hydrogen hydroxy, alkoxy, aralkoxy, alkynyloxy, alkenyloxy, halo acyloxy or acyloxy, provided that when $R_4$ is hydroxy, then at least one of $R_3$ or $R_5$ is other than hydrogen; or
$R_3$ and $R_4$ together are carbonyldioxy, methylenedioxy or ethylenedioxy and form a 5 or 6 membered heterocyclic ring fused to the phenyl ring; provided that at least one of $R_3$, $R_4$ and $R_5$ is other than hydrogen and that $R_3$, $R_4$ and $R_5$ are not all hydroxy;
and the nontoxic pharmaceutically acceptable salts thereof.

Preferred compounds within the scope of Formula II are described below and are those compounds wherein the meta position on the phenyl group is substituted.

One particular advantage of this invention, among others, is that a relatively quick reduction in blood pressure may be effected in a patient after administration of compounds according to Formula I. Another advantage of this invention is that compounds according to Formula I, which have particular substituents in the meta and/or para positions of the phenyl rings, selectively induce blood pressure reduction after either oral or parenteral administration.

DETAILED DESCRIPTION OF THE INVENTION

A preferred class of compounds according to Formula II above is where:
R is hydrogen;

R' is lower alkyl;

R$_1$, R" and R'" are as defined above;

R$_2$ and R$_6$ are the same or different and are lower alkyl, lower alkoxy or halo;

and at least one of R$_3$, R$_4$ and R$_5$ is hydroxy, ar-loweralkoxy, lower alkyl acyloxy, or lower alkoxy, provided that when R$_4$ is hydroxy, then at least one of R$_3$ or R$_5$ is other than hydrogen.

Compounds of this invention, of particular interest, include the subclasses in which the R, R', R", R'", R$_1$, R$_2$ and R$_6$ substitutions are the substitutions noted above and where:

R$_4$ is lower alkoxy, benzyloxy, 2-phenethoxy, or acetoxy, when R$_3$ and R$_5$ are each hydrogen;

R$_3$ is hydroxy, benzyloxy, 2-phenethoxy, acetoxy, or lower alkoxy when R$_4$ and R$_5$ are each hydrogen;

R$_3$ and R$_4$ are hydroxy, lower alkylacyloxy, ar-loweralkoxy, or lower alkoxy when R$_5$ is hydrogen; and R$_3$ and R$_5$ are hydroxy or lower alkoxy when R$_4$ is hydrogen.

Another embodiment of this invention of particular interest, comprises compounds of Formula I where R$_3$ and R$_4$ together form a carbonyldioxy or alkylenedioxy group such as shown in Formula IIa or IIb.

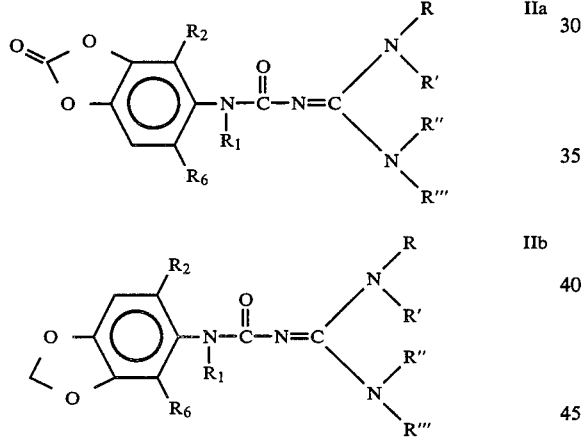

A preferred subclass of compounds according to Formula II is where:

R$_2$ and R$_6$ are lower alkyl or halo;

R$_1$ is hydrogen;

and at least one of R$_3$, R$_4$ and R$_5$ is hydroxy, methoxy or ethoxy, provided that when R$_4$ is hydroxy at least one of R$_3$ or R$_5$ is other than hydrogen.

Compounds of Formula I can exist in enolized or tautomeric forms or may be obtained as hydrates or in different polymorphic forms. One form may predominate over another depending upon the degree and location of substitution, and, if in solution, on the nature of the solvent. The rates of conversion of one tautomer to another will depend upon the nature of the solvent, the degree of hydrogen bonding permitted, the temperature and possibly other factors (such as pH, trace impurities and the like).

To illustrate what is meant by this, a number of likely structures are here shown for just one of the compounds of this invention.

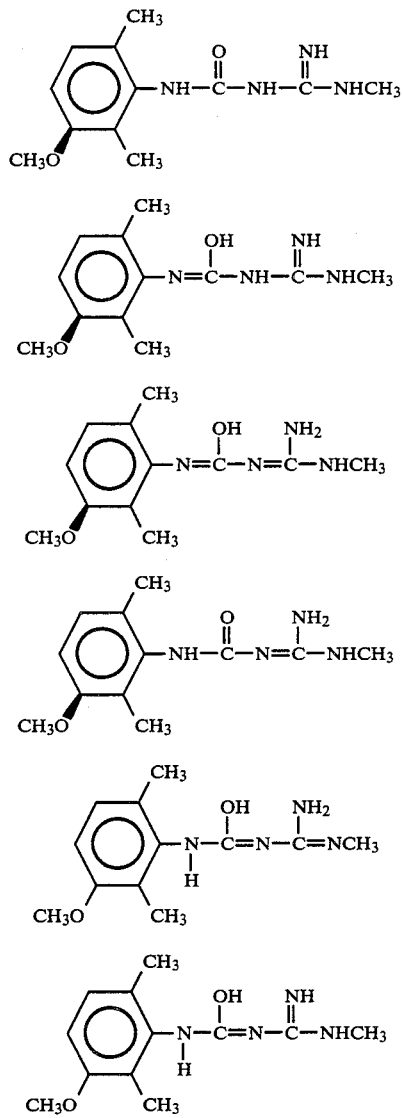

Of course, other types of structures are possible such as those with hydrogen bonding.

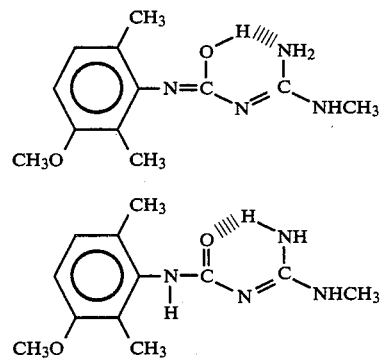

The structures given above are representative of this kind of phenomenon and are encompassed within the scope of this invention. It is predictable that in physiological conditions, any one or all of these structures may exist or even predominate at the sites at which these molecules operate.

It is understood that the designations of the amidinoureas suitable for use in the practice of this invention are intended to include the compounds specifically named or shown by structure along with the alternative or transient states where such exist. It is also intended to include the pharmaceutically acceptable salts of the amidinoureas designated by Formula I. Such salts include the nontoxic addition salts.

It is generally accepted in the pharmacological arts that nontoxic acid addition salts of pharmacologically active amine compounds may be readily prepared from their free bases, without loss of activity. The salts merely provide a convenient solubility factor. The amidinoureas of this invention may be readily converted to their nontoxic acid addition salts by customary methods in the art. The nontoxic salts of this invention are formed from acids which are pharmacologically acceptable in the intended dosages. The nontoxic salts may be prepared from inorganic acids, and organic acids, including higher fatty acids, higher molecular weight acids, etc. Exemplary acids are hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

The nomenclature applied to the compounds of this invention is as follows:

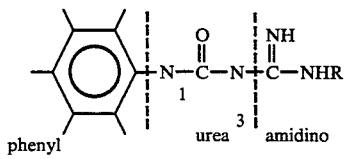

As employed above and throughout the disclosure, the following terms, unless otherwise indicated, shall be understood to have the following meanings.

"Alkyl" means a saturated aliphatic hydrocarbon which may be either straight- or branched-chain. Alkyl groups which have no more than about 12 carbon atoms are preferred and may be methyl, ethyl and structural isomers of propyl, butyl, pentyl, hexyl, heptyl, octyl, nonyl, decyl, undecyl and dodecyl. Also included are the cycloalkyl groups such as cyclopropyl, cyclopentyl, cyclohexyl, etc., and the cycloalkylakyl groups such as cyclopropylmethyl and the like.

"Lower alkyl" means an alkyl group as above, having 1 to 6 carbon atoms. Suitable lower alkyl groups are methyl, ethyl, n-propyl, isopropyl, butyl, isobutyl, sec-butyl, tert butyl, n-pentyl, isopentyl and neopentyl.

The terms "halo" and "halogen" include all four halogens, namely, fluorine, chlorine, bromine and iodine. The halo alkyls include groups having more than one halo substituent which may be the same or different, such as trifluoromethyl, 1-chloro-2-bromo-ethyl, etc.

"Aryl" means phenyl or phenyl in which one or more of the phenyl hydrogens has been replaced by the same or different substituents selected from the group consisting of halo, lower alkyl, halo-lower alkyl, nitro, amino, lower alkanoyl, hydroxy, lower hydroxy, phenyl-lower alkoxy, lower alkanoyl, cyano, halo-lower alkoxy, and lower alkyl sulfonyl.

"Alkoxy" is intended to include hydroxy alkyl groups. Preferred lower alkyl groups such as methoxy, ethoxy, n-propoxy, i-propoxy, and the like.

"Aralkoxy" means an alkoxy group as above substituted with an aryl group. Preferred aralkoxy groups are arloweralkoxy groups such as, benzyloxy, 2-phenethoxy, etc.

The preferred "halo lower alkyl" group is trifluoromethyl.

The preferred "halo lower alkoxy" group is trifluoromethoxy.

The compounds of this invention may be prepared by the following general synthesis.

Condensation of a substituted phenyl isocyanate (prepared from an aniline and phosgene in the customary manner) with an N-alkyl substituted guanidine results in a 1-substituted phenyl-3-N-alkyl-amidinourea. The reaction is carried out in a polar media using solvents such as alcohol, tetrahydrofuran, etc. It is convenient to carry out the reaction by preparing the isocyanate in the reaction media and then forming the N-alkyl guanidine in situ by hydrolyzing the N-alkyl guanidine acid addition salt with base. Condensation of the isocyanate takes place when the guanidine forms and the amidinourea compound results. (Scheme I)

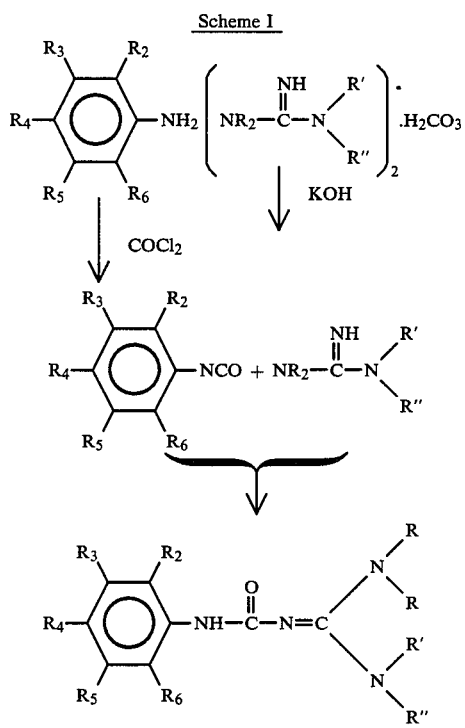

The amidinourea compounds may also be prepared by degradation of the corresponding biguanide. When a 1-substituted phenyl-N-alkyl biguanide compound is hydrolyzed in acid at elevated temperature, then the resultant product is 1-substituted phenyl-3-N-alkylamidinourea. (Scheme II) This reaction is preferably carried out using hydrochloric acid. The reaction time and reaction temperature will depend on the particular biguanide used and the concentration of the acid present. In general, the more concentrated acids will not require high temperatures or long periods of reaction time.

Scheme II

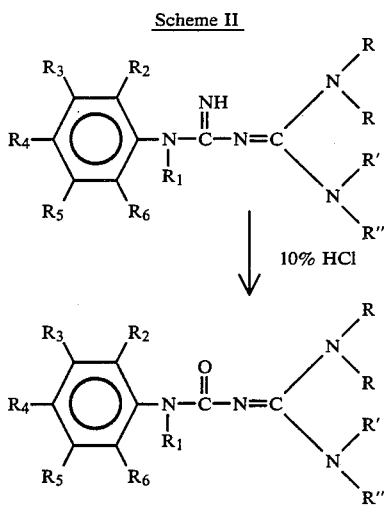

The introduction of R, R', R", and R₁ to R₆ substituents into the phenyl amidinourea structure may be effected by choosing appropriately substituted starting materials. For example, when R₁ substitution is desired the starting material can be an aniline having N-alkyl substitution. Reaction with phosgene results in the aniline acid chloride which is then reacted with the N-alkyl guanidine to prepare the amidinourea. (Scheme III)

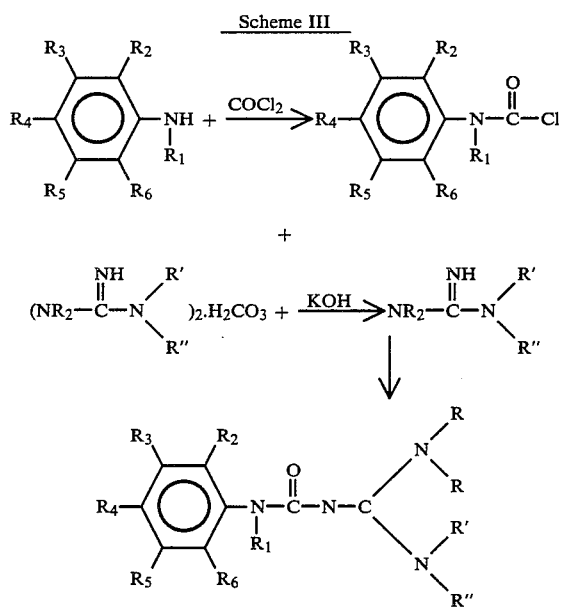

Substitution in the meta or para positions of the phenyl moiety may be accomplished either before or after the amidinourea is formed. Substitution of the phenyl group may be accomplished by any means known to those skilled in the art including the use of an appropriate enzyme reagent, such as, a hydroxylase.

It is preferred that the starting aniline contain any hydroxy groups which may be desired in the amidinourea final product. These hydroxy groups may be in protected form, i.e., in the form of the corresponding acyloxy or aralkyloxy group, and may be prepared in the usual fashion by acylating the starting hydroxy aniline compound with acyl halide or anhydride in the presence of base or by aralkylating with an aralkyl halide or sulfate while the amine function is protected in the customary manner. Hydrogenolysis of the aralkyl compound to the desired hydroxy compound may then take place after the formation of the amidinourea. This may be accomplished with a metal catalyst (Pd/C, Pt etc.) in a polar medium (ethanol, THF, etc.) or sodium in liquid ammonia etc. Thus, for example, 1-(3,4-dihydroxy-2,6-dimethylphenyl)-3-methyl amidinourea compound may be prepared from the corresponding 3,4-dibenzyloxy-2,6-dimethylaniline. Analogously, the hydroxy compounds may also be prepared by hydrolysis of the acyl derivatives with acid.

The starting hydroxy or alkoxy anilines or protected hydroxy anilines are either known, or may be prepared by known techniques. For example, aryl compounds may be hydroxylated according to methods noted in "Compendium of Organic Synthetic Methods", Harrison and Harrison (John Wiley & Sons 1971) section 41, hereby incorporated by reference. See also, "Reagents for Organic Synthesis", Fieser and Fieser, Vol. 1 at page 474.

4-hydroxy-2,6-disubstituted anilines may be prepared starting from the 3,5-disubstituted phenol by forming the 4-nitroso phenol which is further oxidized to the 4-nitrophenol. The phenolic hydroxy group may then be masked by an appropriate protecting group and the nitro compound reduced to the desired aniline. The following schematic reaction sequence illustrates this general synthesis.

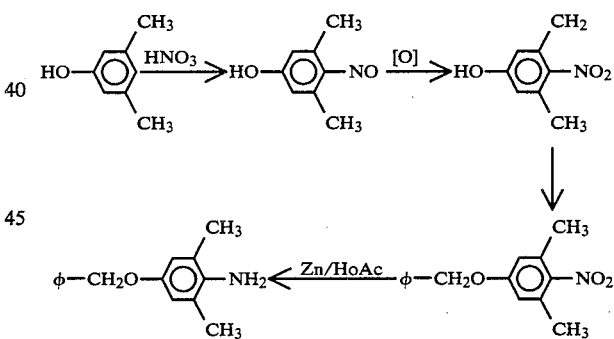

3-hydroxy-2,6-disubstituted anilines may be prepared as depicted in the following sequence starting from a 2,6-disubstituted nitrobenzene. Nitrating meta to the nitro substituent followed by selective reduction yields an amino group which is then converted to the desired hydroxy substituent.

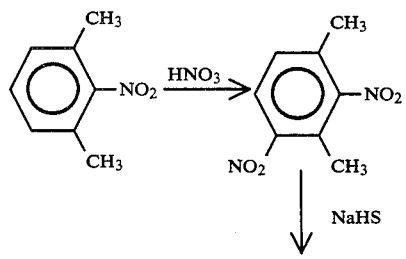

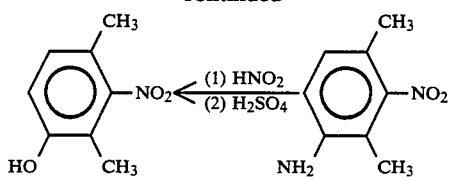

3,4-dihydroxy-2,6-disubstituted anilines may be prepared from a 3,4-methylenedioxy aniline by halogenating the 2 and 6 positions of the aniline and deprotecting the 3 and 4 positions. The aniline may be utilized in its protected form and deprotected after the amidinourea is formed.

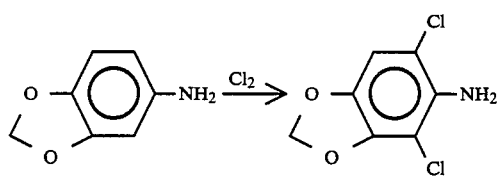

3,4-dibenzyloxy, or a 3,4-dimethoxy aniline may also be utilized and 2,6-dimethyl substitution effected according to the following general scheme.

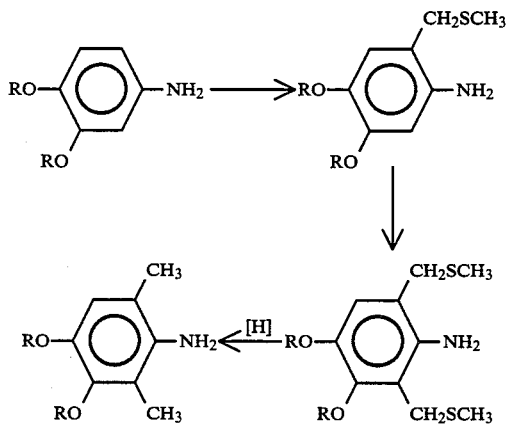

The preparation of other 3-, 4- and 5-substituted anilines will be readily apparent to those skilled in the art.

Phenyl substitution may also be carried out at other stages of synthesis depending on the substituents present and the substituents desired. Various combinations of the foregoing reactions can be determined by one skilled in the art in order that the desired product results. Thus, a phenylamidinourea may be halogenated or nitrated as above, etc.

The biguanide starting materials are also either known, or may be prepared by known procedures. The following general synthesis may be used.

Condensation of N-cyano-N'-alkylguanidine and a protected hydroxylated aniline in the presence of an equimolar amount of a mineral acid results in the corresponding phenylbiguanide.

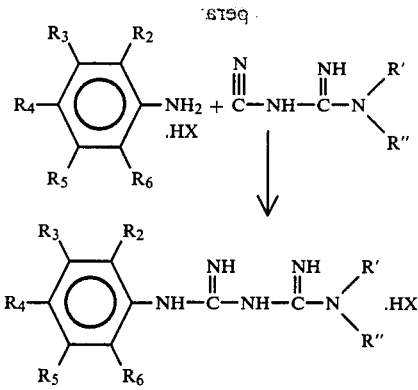

This reaction is preferably carried out on the aniline salt either in a polar media or neat and using increased temperatures. The appropriately substituted product may be prepared by the reactions above when these are also carried out on the biguanide.

The following are detailed examples which show the preparation of the compounds of this invention.

EXAMPLE I

The preparation of 1-(2,6-dimethyl-4-benzyloxyphenyl)-3-methyl amidinourea

Step 1

3,5-dimethyl-4-nitrosophenol 750 ml of concentrated HCl are added to a solution of 3,5-dimethyl phenol (80.6 g) in 750 ml of 95% ethyl alcohol. The mixture is cooled to 0° C. in an ice/methanol bath. While maintaining the temperature of the reaction mixture below 5° C. a solution of $NaNO_2$ (69.0 g) in 150 ml of $H_2O$ is added dropwise to the reaction mixture. The mixture is stirred at 0° C. for more than an hour and then poured into 9 liters of water. The aqueous mixture is filtered to give a yellow solid which is recrystallized from hot methanol and filtered to give 71.45 grams of a yellow solid, M.P. 180°–181° C. (dec).

Step 2

3,5-dimethyl-4-nitrophenol

A mixture of 3,5-dimethyl-4-nitrosophenol (70.63 g), and$(NH_4)_6Mo_7O_{24}\cdot 4H_2O$ (2.83 g) in 770 ml of glacial acetic acid is warmed on a steam bath. 30% $H_2O_2$ (84 ml) is added to the mixture in 10 ml portions until an exothermic reaction is observed. The reaction mixture is then stirred and the remainder of the $H_2O_2$ solution added in small portions. The reaction mixture is heated and stirred until a clear dark red solution results. A yellow-orange solid percipitated from the solution after stirring for another 20–30 minutes. The reaction mixture is stirred overnight and filtered to give a small amount of a yellow solid and a clear dark red filtrate. The red filtrate is concentrated in vacuo and partitioned between $H_2O$ and ether. The aqueous layer is washed with ether and the combined ether extracts washed with 10% sodium carbonate until the aqueous layer becomes basic. The ether extract is dried, filtered, and concentrated in vacuo to a yellow-orange solid. The solid is dissolved in hot toluene, filtered, concentrated and allowed to cool overnight. After cooling in an ice bath the mixture is filtered to give 49.5 grams of a yellowgreen solid identified as 3,5-dimethyl-4-nitrophenol, M.P. 106°–108° C.

Step 3

5-benzyloxy-2-nitro-meta-xylene

A mixture of 3,5-dimethyl-4-nitrophenol (17.6 g), benzyl chloride (20.0 g) and anhydrous $K_2CO_3$ (13.2 g) in acetone (100 ml) is stirred under reflux for 22 hours. The reaction mixture is filtered and the precipitate washed with acetone. The acetone extract is concentrated in vacuo and the residue short path distilled (160°–170° C; 50μ) to give 22.9 grams of an orange liquid which crystallized on standing.

Step 4

4-benzyloxy-2,6-dimethylaniline

Zinc dust is added to a solution of 5-benzyloxy-2-nitro-m-xylene (22.9g) in 250 ml of glacial acetic acid. The reaction mixture is stirred until the solution is colorless. The reaction mixture is cooled, filtered through Celite to remove excess zinc and the filtrate diluted with $H_2O$ and cooled with ice. $NH_3$ is added to make the solution slightly alkaline followed by small amount of sodium hydrosulfite. The product is filtered, dissolved in methylene chloride, dried and concentrated to give 18.3 grams of a tan solid.

Step 5

4-benzyloxy-2,6-dimethylphenyl isocyanate

Excess $COCl_2$ is bubbled into a solution of 4-benzyloxy-2,6-dimethylaniline (18.3 g) in toluene (250 ml). The reaction mixture is brought to reflux and approximately 200 ml of toluene is distilled off. The reaction mixture is concentrated in vacuo to give a brown solid which is vacuum distilled (T=170°–185° C.) to give 17.0 grams of the desired product.

Step 6

1-(4-benzyloxy-2,6-dimethylphenyl)-3-methylamidinourea hydrochlorid 6.4 grams of a 50% aqueous sodium hydroxide solution are added to a stirred suspension of methylguanidine sulfate (9.8 g) in THF (100 ml). After stirring for one hour, 10 grams of anhydrous $Na_2SO_4$ are added and the mixture stirred for an additional hour. 4-benzyloxy-2,6-dimethylphenyl isocyanate (10.1 g) in THF (30 ml) is slowly added dropwise to the reaction mixture which is allowed to stir overnight. The THF is removed in vacuo and the residue partitioned between chloroform and water. The aqueous layer is extracted with chloroform and the organic extracts dried and concentrated. The residue is dissolved in chloroform and acidified with HCl/ether. The solvents are removed by vacuum and the gummy foam crystallized from methanol/acetonitrile to give 12.1 grams of the hydrochloride salt, M.P. 206°–8° C.

EXAMPLE II

The preparation of 1-(3-hydroxy-2,6-dimethylphenyl)-3-methyl amidinourea

Step 1

1,3-dimethyl-2,4-dinitrobenzene 1,3-dimethyl-2-nitrobenzene (151.2 g) is dissolved in 500 ml of $CH_2Cl_2$ and cooled to below 0° C. in a methanol ice bath. Sulfuric acid (200 ml) is added dropwise maintaining a temperature at below 0° C. After the sulfuric acid addition is complete, fuming nitric acid (86 ml) is added dropwise at a rate which maintains the temperature between −5° to −2° C. After the addition is complete the mixture is stirred at −3° to −5° C. for 2 hours. 200 ml of water are carefully added to the aqueous acidic layer and after cooling to room temperature is extracted with 600 ml of $CH_2Cl_2$. The extracts are combined and washed with 600 ml of $H_2O$ saturated NaCl solution and dried overnight. The mixture is filtered and the filtrate concentrated to give 192.2 grams of a yellow solid, M.P. 81°–83° C.

Step 2

2,4-dimethyl-3-nitro aniline (a) Preparation of sodium sulfide reducing agent $Na_2S$ is dissolved in 750 ml of $H_2O$ and cooled in an ice water bath. Sodium bicarbonate is added at a rate so that the temperature does not exceed 15° C. The reaction mixture is stirred after the addition is complete and 800 ml of methanol is added so that the temperature does not exceed 25° C. and stirred for 15 min. The reaction mixture is filtered.

(b) Reduction of nitro aniline

The filtrate from above is added to a solution of 128.75 gram of 1,3-dimethyl-2,4-dinitrobenzene in approximately one liter of methanol, heated to reflux for one and one half hours, and stirred at room temperature overnight. The mixture is refluxed until all starting material has been consumed. Additional reducing agent is added if needed. The reaction mixture is filtered and the filtrate concentrated. One liter of water is added, stirred, filtered and the precipitate is washed with water and dried to give 105.6 grams of a yellow solid, M.P. 78°–79° C.

Step 3

2,4-dimethyl-3-nitrophenol 2,4-dimethyl-3-nitroaniline (105.6 g) is added to a reaction mixture containing 300 ml of $H_2SO_4$ and 300 ml of $H_2O$. The reaction mixture is stirred at a temperature of 105°–108° C. for one half hour and then cooled to 0° C. A solution of sodium nitrite (52.6 g) in $H_2O$ (124 ml) is added dropwise. After addition is complete the reaction mixture is poured into a 50% aqueous $H_2SO_4$ solution (2,000 ml) and refluxed for one and one half hours. The reaction mixture is cooled over the weekend to an ambient temperature, and filtered leaving a yellow and black solid which is washed with $H_2O$, dried and boiled with hexanes (8 l). The hexane extract is concentrated and filtered to obtain 65.4 grams of a yellow solid, M.P. 99°–101° C.

Step 4

4-benzyloxy-2-nitro-m-xylene 56.6 grams of 2,4-dimethyl-3-nitrophenol, 64.5 grams of benzyl chloride and 74.6 grams of anhydrous $K_2CO_3$ are stirred under reflux for 24 hours. The reaction mixture is filtered through a pad of celite and the celite washed with acetone. The filtrate is concentrated in vacuo and the residue vacuum distilled to give 83.9 grams of the benzyloxy xylene (B.P. 150°–160° C., 50μ). The material solidified on standing.

Step 5

3-benzyloxy-2,6-dimethylaniline

Zinc dust is added in portions to a solution of 4 benzyloxy-2-nitro-m-xylene (83.8 g) in glacial acetic acid (715 ml) Addition is complete when the exothermic reaction subsides. The reaction mixture is filtered through celite and the pad washed with acetic acid. The filtrate is concentrated in vacuo and the residue diluted with $H_2O$ and made basic with ammonium hydroxide, and extracted with chloroform. The combined organic extracts are dried and concentrated in vacuo to give the desired aniline in quantitative crude yield.

Step 6

3 benzyloxy-2,6-dimethylphenyl isocyanate

Excess phosgene is bubbled into a solution of 3-benzyloxy-2,6-xylidene (74.9 g) in 750 ml of toluene. The reaction mixture is heated at reflux and after the reaction mixture clarified 500 ml of toluene is removed by distillation at atmospheric pressure. The remaining toluene is removed in vacuo. The residue is distilled in vacuo to give an orange-brown liquid (B.P. 160°–175° C. 50μ).

Step 7

1-(3-benzyloxy-2,6-dimethylphenyl)-3-methylamidinourea hydrochlorid 16 grams of a 50% aqueous sodium hydroxide solution are added to a suspension of methyl guanidine sulfate (24.4 g) in THF (400 ml). The mixture is stirred for 1 hour and 25 g of anhydrous $Na_2SO_4$ are added after which the mixture is stirred an additional one half hour. 3-benzyloxy-2,6-dimethylphenyl isocyanate (25.3 g) in THF (200 ml) is added to the reaction mixture over a 5 hour period and the reaction mixture stirred overnight. The reaction mixture is filtered and the solid washed with THF. The filtrate is concentrated in vacuo and the residue partitioned between methylene chloride and water. The aqueous layer is extracted with additional methylene chloride and the combined extracts dried, filtered and made acidic with HCl/methanol. The extract is evaporated in vacuo and the residue crystallized from methanol/acetonitrile. Recrystallization from methanol/acetonitrile, filtering and drying under vacuum results in 30.6 grams of the desired hydrochloride salt as a white solid, M.P. 189.5°–191° C.

Step 8

1-(2,6-dimethyl-3-hydroxyphenyl)-3-methylamidinourea hydrochloride 1-(3-benzyloxy-2,6-dimethylphenyl)-3-methylamidinourea hydrochloride (18.2 g) and 5% Pd/C (1.0 g) in absolute ethanol (200 ml) containing HCl/methanol (50 ml) are shaken under an atmosphere of $H_2$ (50 psi) for 45 minutes. The reaction mixture is filtered through Celite and the filtrate is concentrated. in vacuo. The resulting solid is crystallized from methanol/acetonitrile to give after drying 12.3 grams of the desired amidinourea hydrochloride salt as a white powder, M.P. 224°–5° C. (dec).

EXAMPLE III

Preparation of 1-(2,6-dimethyl-4-methoxyphenyl)-3-amidinourea hydrochloride.

Step 1

3,5-dimethyl-4-nitroanisole 3,5-dimethyl-4-nitrophenol (33.43 g), methyl p-toluene sulfonate (40.97 g) and $K_2CO_3$ (31.79 g) are stirred at reflux in 200 ml of acetone for four and one half hours and then stirred at R.T. overnight. The reaction mixture is filtered to give a dark amber filtrate. The filtrate is concentrated in vacuo to a yellowish brown solid which is dissolved in ethyl acetate washed with saturated aqueous sodium chloride, dried and concentrated in vacuo. The concentrate is distilled (87°–104° C./0.10 mm) to give a yellow waxy looking solid. The solid is dissolved in hot ethanol and recrystallized, M.P. 50°–52° C.

Step 2

2,6-dimethyl-4-methoxyaniline hydrochloride 150 ml of glacial acetic acid are cautiously added dropwise to a refluxing mixture of 3,5-dimethyl-4-nitroanisole (32.4 g) and 47.07 grams of zinc dust in 100 ml of toluene. The reaction is allowed to reflux for another two hours and allowed to cool. The reaction mixture is filtered and concentrated in vacuo to a dark oil which is taken up in 400 ml of $CH_2Cl_2$ and washed with 50 ml of concentrated ammonium hydroxide and 800 ml of water. The organic layer is dried, filtered and concentrated in vacuo. The resulting dark oil is dissolved in ether. $HCl/Et_2O$ is added to form a precipitate which is collected and dried to give 29.28 grams of the aniline hydrochloride, M.P. 228°–232° C.

Step 3

2,6-dimethyl-4-methoxy-phenyl isocyanate

Phosgene gas (distilled from 23 ml of liquid) is bubbled into a solution of 2,6-dimethyl-4-methoxyaniline hydrochloride (28.5 g) in 400 ml of toluene. The reaction mixture is refluxed until the reaction is complete. About 300 ml of toluene are removed by distillation and the remainder concentrated in vacuo leaving a dark oil which is distilled to give 21.46 grams of a clear yellow liquid (75°–84° C./70μ).

Step 4

1-(2,6-dimethyl-4-methoxyphenyl)-3-methylamidinourea hydrochloride 7.22 grams of a 50% aqueous sodium hydroxide solution are added to a stirred mixture of methyl guanidine sulfate (9.76 g) in 200 ml of THF. The mixture is stirred for one half hour followed by the addition of anhydrous $Na_2SO_4$ (10 g). The mixture is stirred for an additional one half hour. 8.0 grams of 2,6-dimethyl-4-methoxyphenyl isocyanate in 50 ml of THF are added dropwise to the reaction mixture and the mixture stirred overnight. The reaction mixture is filtered and concentrated in vacuo to obtain a yellow oil. The yellow oil is taken up in methylene chloride and water. The methylene chloride layer is dried, filtered and concentrated in vacuo leaving an off-white solid which is dissolved in HCl-methanol, filtered and concentrated in vacuo to a yellow oil which is dissolved in ethyl acetate and methanol and recrystallized to give 7.53 grams of a white solid, M.P. 221°–224° C.

EXAMPLE IV

Preparation of 1-(2,6-dimethyl-3-methoxyphenyl)-3-methyl amidinourea hydrochloride.

Step 1

2,4-dimethyl-3-nitroanisole

A mixture of 32.12 grams of 2,4-dimethyl-3-nitrophenol, 35.78 grams of methyltosylate and 28.5 grams of anhydrous $K_2CO_3$ in 200 ml of acetone is heated to reflux for 12 hours. The reaction mixture is filtered leaving a tan solid. The filtrate is concentrated in vacuo. The concentrated filtrate is taken up in ethyl acetate and washed with 10% aqueous sodium hydroxide solution and saturated aqueous sodium chloride. The remaining ethyl acetate layer is dried, filtered and concentrated in vacuo to give a dark oil which is distilled (T=80°–87° C./50μ) to give 30.95 grams of a yellow solid which is recrystallized from absolute ethanol, M.P. 53°–55° C.

Step 2

2,6-dimethyl-3-methoxyaniline hydrochloride 30.0 grams of 2,4-dimethyl-3-nitroanisole and 44.45 grams of zinc metal dust are refluxed in 100 ml of toluene. 150 ml of glacial acetic acid are cautiously added dropwise to the reaction mixture. The reaction mixture is refluxed for two and one half hours after the addition of glacial acetic acid is complete and allowed to sit over the weekend. The reaction mixture is filtered and the filtrate concentrated in vacuo. The resulting dark oil is taken up in 400 ml of methylene chloride and washed with 50 ml of concentrated ammonium hydroxide and 800 ml of water. The methylene chloride solution is dried, filtered and concentrated in vacuo to give a dark oil. The oil is dissolved in ether and the ether solution acidified with HCl/ether. The methoxy aniline hydrochloride salt is obtained as 27.4 grams of a purple precipitate, M.P. 216°–221° C.

Step 3

2,6-dimethyl-3-methoxyphenyl isocyanate 29.68 grams of phosgene gas are bubbled into a stirred mixture of 26.3 grams of 2,6-dimethyl-3-methoxyaniline hydrochloride in 450 ml of chlorobenzene. The reaction mixture is refluxed for one hour after bubbling in the 20% NaOH trap ceases. The reaction mixture is concentrated in vacuo to a dark oil and the dark oil distilled (70°–77° C./50μ) to give 19.46 grams of the isocyanate as a yellow liquid.

Step 4

1-(2,6-dimethyl-3-methoxyphenyl)-3-methylamidinourea hydrochloride 5.08 grams of a 50% aqueous sodium hydroxide solution are added to a stirred mixture of methyl guanidine sulfate (6.2 g) in 120 ml of THF. The mixture is stirred for one half hour and 5.62 grams anhydrous $Na_2SO_4$ are added and the mixture stirred for an additional one half hour. 2,6-dimethyl-3-methoxyphenyl isocyanate (4.5 g) in 30 ml of THF is slowly added dropwise to the reaction mixture and stirred over the weekend. The reaction mixture is filtered and concentrated in vacuo and the resulting yellow oil partitioned between methylene chloride and water. The methylene chloride layer is dried, filtered and concentrated in vacuo to give an off white solid which is taken up in methanol. HCl/methanol is added to the solution which is concentrated in vacuo. The salt is crystallized from 100 ml of ethyl acetate/methanol to yield 4.58 grams of the hydrochloride salt, M.P. 194 5°–196° C.

Various tests can be carried out in animal models to show the ability of the compounds of this invention to produce blood pressure lowering action in animals and are known to correlate well with blood pressure lowering activity in humans. These are considered to be standard tests used to determine antihypertensive properties.

Determination of Antihypertensive Activity

A description of the test protocol used in the determination of the antihypertensive activity of the compounds of this invention follow.

(a) Male spontaneously hypertensive rats (SHR's) eleven weeks old, weighing 200–220 grams, are chosen for testing. The average systolic blood pressure (as measured below) should be 165 mmHg or above. Any rat not initially meeting this criterion is not utilized.

(b) A Beckman dynograph is balanced and calibrated using a Beckman indirect blood pressure coupler. A mercury monometer is placed on one arm of the glass "T" tube. The known pressure head in the tail cuff is synchronized with the recorder output so that 1 mm pen deflection=5 mmHg. Any correction is made using the chart calibration screw on the pressure coupler. The pulse amplitude is controlled by the pre-amplifier using a 20 v/cm setting.

The rats are prewarmed in groups of five for twenty minutes to dilate the tail artery from which the arterial pulse is recorded. After prewarming, each rat is placed in an individual restraining cage with continued warming. When the enclosure temperature has been maintained at 35° C. for 5 minutes, recordings are started. The tail cuff is placed at the base of the rat's tail and the rubber bulb of the pneumatic tail cuff transducer is taped securely to the ventral surface of the tail. When the rat's pulse reaches maximum amplitude and is unwavering, the cuff is inflated and the air slowly released. Systolic blood pressure is read at the point of the chart when the first pulsatile deflection appears on the chart recording while the air in the cuff is being released. The exact point of the systolic blood pressure reading is where the first deflection forms a 90° angle to the falling cuff pressure base line. After obtaining nine or ten consistent readings, the average of the middle five readings is calculated.

(c) Three groups of five to twenty rats receive the test compound at doses of about 25 mg/kg p.o. A fourth group of five to twenty control rats receives distilled water. Statistical comparisons of systolic pressure (four hours after the first dose and sixteen hours after the second dose) are made on a daily basis using the Student t test for dependent variables (see, E. Lord, Biometrika, 34, 56 (1947), with the predose observations serving as baseline values for each rat.

In addition to the blood pressure screening described above, certain of these compounds have undergone further studies. Utilizing standard laboratory techniques, the effect that these compounds have on blood pressure has been observed following the administration of solutions containing the phenyl amidinoureas into the vertebral artery in dogs and into the lateral cerebral ventricle in rats.

In view of the results of these tests, the meta and para substituted 2,6-disubstituted phenyl amidinourea compounds of this invention possess blood-pressure-lowering activities and are useful as anti-hypertensive agents.

The results of these tests indicate that, in general, the substituted phenyl amidinoureas according to this invention effect an acute reduction in blood pressure in the test subject. In addition, it has been found that blood pressure may be reduced by either the oral or the parenteral route depending on the meta or para substitution on the amidinourea phenyl group.

In applicants' copending Ser. No. 280,786, assigned to the same assignee as the present application, applicants disclose that the meta- or para- hydroxy substituted phenyl amidinoureas, in general, exhibit good blood pressure lowering activity when administered parenterally in rats, but are ineffective when administered orally, for example, at a dose level of about 25 mg/kg or more. In contrast, the meta-alkoxy phenylamidinoureas disclosed in the '786 application are preferred blood pressure lowering compounds for administration by the oral route. At a dose level of 1 mg/kg in the rat, the meta-methoxy phenylamidinoureas effectively reduce blood pressure while the para-methoxy phenyl amidinourea isomer is inactive. The para-methoxy isomers do not possess a blood pressure lowering effect up to a dose of about 25 mg/kg.

However, it has also been found that N-alkyl substitution effects the blood pressure reducing properties of the oxy substituted phenyl amidinoureas. For example, the 1-oxyphenyl-3-N-alkylamidinoureas of the present invention, in general, do not exhibit oral blood pressure reducing properties when the only oxy substituent is a meta alkoxy substituent. Furthermore, oral blood pressure lowering activity also appears to be absent in compounds having either only a para alkoxy or a meta hydroxy substituent. Surprisingly, oral blood pressure reducing properties are exhibited when the phenyl 3-N-alkylamidinourea compounds of the present invention are para substituted with a hydroxy group. Accordingly, a preferred method for lowering blood pressure in mammalian species comprises the oral administration to a patient of an orally effective amount of an amidinourea compound of the formula

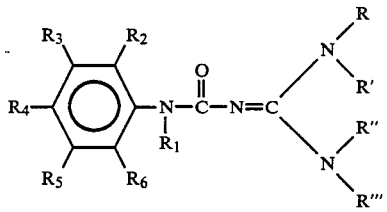

where:
R, R', R", R'" and $R_1$ may be the same or different and and are hydrogen or lower alkyl, provided that at least one of R, R', R" and R'" is other than hydrogen;
$R_2$ and $R_6$ may be the same or different and are lower alkyl, halo, lower alkoxy, halo lower alkyl, nitro, or lower alkylsulfonyl;
$R_4$ is hydroxy;
$R_3$ and $R_5$ may be the same or different and are hydrogen, hydroxy, lower alkoxy, arloweralkoxy, lower alkynyloxy, lower alkenyloxy, halo loweralkyl acyloxy or loweralkyl acyloxy;
provided that $R_3$, $R_4$ and $R_5$ are not all hydroxy; and wherein:
arloweralkoxy means lower alkoxy substituted with phenyl or phenyl in which one or more of the phenyl hydrogens has been replaced by the same or different substituents selected from the group consisting of halo, lower alkyl, halolower alkyl, nitro, amino, lower alkanoyl, hydroxy, lower hydroxy, phenyl-lower alkoxy, lower alkanoyl, cyano, halolower alkoxy, and lower alkyl sulfonyl;
or a nontoxic pharmaceutically acceptable salt thereof.

The most preferred orally effective 1-(phenyl)-3-N-alkylamidinourea compound is 1-(2,6-dimethyl-4-hydroxyphenyl)-3-N-methylamidinourea.

The amidinoureas according to Formula I may be administered orally, parenterally or rectally. The orally active compounds described above are readily absorbed into the bloodstream from the gut and are relatively nontoxic.

When the compounds of Formula I are administered orally, they may be administered in tablets, hard or soft capsules, aqueous or oily suspensions, dispersible powders or granules, emulsions, syrups or elixirs.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc., in order to provide a pharmaceutically appealing and palatable preparation.

Further, the active amidinourea may be administered alone or in admixture with other agents having the same or different pharmacological properties. The compositions may contain selected excipients such as, for example: inert diluents, such as calcium carbonate, lactose, etc; guanulating and distintegrating agents, such as magnesium stearate, etc.; binding agents such as starch, gelatin, etc.; suspending agents such as methylcellulose, vegetable oil, etc.; dispersing agents such as lecithin, etc.; thickening agents such as beeswax, hard parafin, etc.; emulsifying agents such as naturally occurring gums, etc.; non-irritating excipients such as cocoa butter, polyethylene glycols, etc.; and the like.

Further, in formulating these compounds, for every 100 parts by weight of the composition, there may be present between about 5 and 95 parts by weight of the active ingredient. The dosage unit form will generally contain between about 0.1 mg and about 50 mg of the active ingredient of this invention.

In general, the dosage regimen in carrying out the methods of this invention is that which insures maximum therapeutic response until improvement is obtained, and thereafter, the minimum effective level which gives relief. Generally, the daily dose for adults will be between about 5 and about 50 mg/day total dose.

The dosage amounts used in administering the drug, parenterally or by any other route, can be adjusted as necessary to provide and maintain effective blood pressure levels, for example, when the drug is administered directly by intravenous infusion, the rate of infusion can be adjusted to provide blood levels equivalent to those achieved through oral administration. Generally, oral administration of the orally effective compounds as described above is preferred, though in situations such as malignant hypertension or other emergency situations, i.v. or other forms of administration of the compounds of Formula I may be used.

The optimum dosage, of course, will depend on the particular compound being used and the type and severity of the condition being treated. In any specific case, the appropriate dosage selected will further depend on factors of the patient which may influence response to the drug for example, general health, age, weight, etc. of the subject being treated.

Although the optimum quantities for administration of the compounds of Formula I in accordance with the present invention will depend on the compound employed and the particular type of condition treated, oral dose levels of the preferred orally active compounds when administered to humans in total daily doses of about 0.01 to about 5 mg per kg of body weight, given separately, are particularly useful. The preferred dose range is about 0.1 to about 2/mg/kg/day.

One blood pressure therapy that may be preferred is the administration of a combination of amidinoureas which provides for both an immediate and a slow acting (multiple dose dependent) blood pressure lowering effect. This combined therapy utilizes a formulation containing a meta- or para- substituted phenyl amidinourea according to Formula I plus the slow acting 2,6-disubstituted phenyl N-alkyl amidinourea in which the meta and para positions of the phenyl group are unsubstituted, as described in aforementioned U.S. Pat. No. 4,279,928. The administration of the combined formulation may be by oral, intravenous or other route and, accordingly, the oral therapy will preferably use a 1-(4-hydroxyphenyl)-3-N-alkylamidinourea.

Preferred compounds according to this invention are listed in Table I. These compounds are exemplary of applicant's invention and should not be construed as a limitation thereof.

TABLE I 1-(2,6-dimethyl-4-acetoxyphenyl)-3-(N,N,N',N'-tetramethylamidino)urea
1-(2,6-dimethyl-3-hydroxyphenyl)-3-(N,N,N',N'-tetramethylamidino)urea
1-(2,6-dimethyl-3,4-dihydroxyphenyl)-3-(N,N,N',N'-tetramethylamidino)urea
1-(2,6-dimethyl-3,5-dihydroxyphenyl)-3-(N,N,N',N'-tetramethylamidino)urea
1-(2,6-dimethyl-3,4,5-triacetoxyphenyl)-3-(N,N,N',N'-tetramethylamidino)urea
1-(2,6-dichloro-4-acetoxyphenyl)-3-(N,N,N',N'-tetramethylamidino)urea
1-(2,6-dichloro-3-hydroxyphenyl)-3-(N,N,N',N'-tetramethylamidino)urea
1-(2,6-dichloro-3,4-dihydroxyphenyl)-3-(N,N,N',N'-tetramethylamidino)urea
1-(2,6-dichloro-3,5-dihydroxyphenyl)-3-(N,N,N',N'-tetramethylamidino)urea
1-(2,6-dichloro-3,4,5-triacetoxyphenyl)-3-(N,N,N',N'-tetramethylamidino)urea
1-(2-chloro-6-methyl-3-hydroxyphenyl)-3-(N,N,N',N'-tetramethylamidino)urea
1-(2-chloro-6-methyl-4-acetoxyphenyl)-3-(N,N,N',N'-tetramethylamidino)urea
1-(2-chloro-6-methyl-5-hydroxyphenyl)-3-(N,N,N',N'-tetramethylamidino)urea
1-(2-chloro-6-methyl-3,4-dihydroxyphenyl)-3-(N,N,N',N'-tetramethylamidino)urea
1-(2-chloro-6-methyl-3,5-dihydroxyphenyl)-3-(N,N,N',N'-tetramethylamidino)urea
1-(2-chloro-6-methyl-4,5-dihydroxyphenyl)-3-(N,N,N',N'-tetramethylamidino)urea
1-(2-chloro-6-methyl-3,4,5-triacetoxyphenyl)-3-(N,N,N',N'-tetramethylamidino)urea
1-(2,6-diethyl-4-acetoxyphenyl)-3-(N,N,N',N'-tetramethylamidino)urea
1-(2,6-diethyl-3,4-dihydroxyphenyl)-3-(N,N,N',N'-tetramethylamidino)urea
1-(2,6-diethyl-3,5-dihydroxyphenyl)-3-(N,N,N',N'-tetramethylamidino)urea
1-(2,6-diethyl-3,4,5-triacetoxyphenyl)-3-(N,N,N',N'-tetramethylamidino)urea
1-(2,6-diethyl-3-hydroxyphenyl)-3-(N,N,N',N'-tetramethylamidino)urea 1-(2,6-dimethoxy-4-benzyloxyphenyl)-3-N,N-dimethylamidinourea
1-(2,6-dimethoxy-3-benzyloxyphenyl)-3-N,N-dimethylamidinourea
1-(2,6-dimethoxy-3,4-dibenzyloxyphenyl-3-N,N-dimethylamidinourea
1-(2,6-dimethoxy-3,5-dibenzyloxyphenyl)-3-N,N-dimethylamidinourea
1-(2,6-dimethoxy-3,4,5-tribenzyloxyphenyl)-3-N,N-dimethylamidinourea
1-(2-chloro-6-methoxy-3-benzyloxyphenyl)-3-N,N-dimethylamidinourea
1-(2-chloro-6-methoxy-4-benzyloxypheny)-3-N,N-dimethylamidinourea
1-(2-chloro-6-methoxy-5-benzyloxyphenyl)-3-N,N-dimethylamidinourea
1-(2-chloro-6-methoxy-3,4-dibenzyloxyphenyl)-3-N,N-dimethylamidinourea
1-(2-chloro-6-methoxy-3,5-dibenzyloxyphenyl)-3-N,N-dimethylamidinourea
1-(2-chloro-6-methoxy-4,5-dibenzyloxyphenyl)-3-N,N-dimethylamidinourea
1-(2-chloro-6-methoxy-3,4,5-tribenzyloxyphenyl)-3-N,N-dimethylamidinourea
1-(2,6-diethoxy-4-benzyloxyphenyl)-3-N,N-dimethylamidinourea
1-(2,6-diethoxy-3,4-dibenzyloxyphenyl)-3-N,N-dimethylamidinourea
1-(2,6-diethoxy-3,5-dibenzyloxyphenyl)-3-N,N-dimethylamidinourea
1-(2,6-diethoxy-3,4,5-tribenzyloxyphenyl)-3-N,N-dimethylamidinourea
1-(2,6-diethoxy-3-benzyloxyphenyl)-3-N,N-dimethylamidinourea 1-(2,6-dimethoxy-4-acetoxyphenyl)-3-N,N-dimethylamidinourea
1-(2,6-dimethoxy-3-methoxyphenyl)-3-N,N-dimethylamidinourea
1-(2,6-dimethoxy-3-methoxy-4-hydroxyphenyl)-3-N,N-dimethylamidinourea
1-(2,6-dimethoxy-3,5-dimethoxyphenyl)-3-N,N-dimethylamidinourea
1-(2,6-dimethoxy-3,4,5-trimethoxyphenyl)-3-N,N-dimethylamidinourea
1-(2-chloro-6-methoxy-3-methoxyphenyl)-3-N,N-dimethylamidinourea
1-(2-chloro-6-methoxy-4-benzyloxyphenyl)-3-N,N-dimethylamidinourea
1-(2-chloro-6-methoxy-5-methoxyphenyl)-3-N,N-dimethylamidinourea 1-(2-chloro-6-methoxy-3,4-methylenedioxyphenyl)-3-N,N,-dimethylamidinourea
1-(2-chloro-6-methoxy-3,5-dimethoxyphenyl)-3-N,N-dimethylamidinourea
1-(2-chloro-6-methoxy-4,5-methylenedioxyphenyl)-3-N,N-dimethylamidinourea
1-(2-chloro-6-methoxy-3,4,5-trimethoxyphenyl)-3-N,N-dimethylamidinourea
1-(2,6-diethoxy-4-acetoxyphenyl)-3-N,N-dimethylamidinourea
1-(2,6-diethoxy-3-hydroxy-4-methoxyphenyl)-3-N,N-dimethylamidinourea
1-(2,6-diethoxy-3,5-dimethoxyphenyl)-3-N,N-dimethylamidinourea
1-(2,6-diethoxy-3,4,5-trimethoxyphenyl)-3-N,N-dimethylamidinourea
1-(2,6-diethoxy-3-methoxyphenyl)-3-N,N-dimethylamidinourea
1-(2,6-dimethoxy-4-acetoxyphenyl)-3-N,N'-dimethylamidinourea
1-(2,6-dimethoxy-3-methoxyphenyl)-3-N,N'-dimethylamidinourea
1-(2,6-dimethoxy-3-methoxy-4-hydroxyphenyl)-3-N,N'-dimethylamidinourea
1-(2,6-dimethoxy-3,5-dimethoxyphenyl)-3-N,N'-dimethylamidinourea
1-(2,6-dimethoxy-3,4,5-trimethoxyphenyl)-3-N,N'-dimethylamidinourea 1-(2,6-dimethyl-4-hydroxyphenyl)-1-methyl-3-ethylamidinourea
1-(2,6-dimethyl-3-hydroxyphenyl)-1-methyl-3-ethylamidinourea
1-(2,6-dimethyl-3,4-dihydroxyphenyl)-1-methyl-3-ethylamidinourea
1-(2,6-dimethyl-3,5-dihydroxyphenyl)-1-methyl-3-ethylamidinourea
1-(2,6-dimethyl-3,4,5-trihydroxyphenyl)-1-methyl-3-ethylamidinourea
1-(2,6-dichloro-4-hydroxyphenyl)-1-methyl-3-ethylamidinourea
1-(2,6-dichloro-3-hydroxyphenyl)-1-methyl-3-ethylamidinourea
1-(2,6-dichloro-3,4-dihydroxyphenyl)-1-methyl-3-ethylamidinourea
1-(2,6-dichloro-3,5-dihydroxyphenyl)-1-methyl-3-ethylamidinourea
1-(2,6-dichloro-3,4,5-trihydroxyphenyl)-1-methyl-3-ethylamidinourea
1-(2-chloro-6-methyl-3-hydroxyphenyl)-1-methyl-3-ethylamidinourea
1-(2-chloro-6-methyl-4-hydroxyphenyl)-1-methyl-3-ethylamidinourea
1-(2-chloro-6-methyl-5-hydroxyphenyl)-1-methyl-3-ethylamidinourea
1-(2-chloro-6-methyl-3,4 -dihydroxyphenyl)-1-methyl-3-ethylamidinourea
1-(2-chloro-6-methyl-3,5-dihydroxyphenyl)-1-methyl-3-ethylamidinourea
1-(2-chloro-6-methyl-4,5-dihydroxyphenyl)-1-methyl-3-ethylamidinourea
1-(2-chloro-6-methyl-3,4,5-trihydroxyphenyl)-1-methyl-3-ethylamidinourea
1-(2,6-diethyl-4-hydroxyphenyl)-1-methyl-3-ethylamidinourea
1-(2,6-diethyl-3,4-dihydroxyphenyl)-1-methyl-3-ethylamidinourea
1-(2,6-diethyl-3,5-dihydroxyphenyl)-1-methyl-3-ethylamidinourea
1-(2,6-diethyl-3,4,5-trihydroxyphenyl)-1-methyl-3-ethylamidinourea
1-(2,6-diethyl-3-hydroxyphenyl)-1-methyl-3-ethylamidinourea 1-(2,6-dimethyl-4-ethoxyphenyl)-3-N,N'-diethylamidinourea
1-(2,6-dimethyl-3-methoxyphenyl)-3-N,N'-diethylamidinourea
1-(2,6-dimethyl-3,4-dimethoxyphenyl)-3-N,N'-diethylamidinourea
1-(2,6-dimethyl-3-hydroxy-5-methoxyphenyl)-3-N,N'-diethylamidinourea
1-(2,6-dimethyl-3,4,5-trimethoxyphenyl)-3-N,N'-diethylamidinourea
1-(2,6-dichloro-4-benzyloxyphenyl)-3-N,N'-diethylamidinourea
1-(2,6-dichloro-3-methoxyphenyl)-3-N,N'-diethylamidinourea
1-(2,6-dichloro-3-methoxy-4-hydroxyphenyl)-3-N,N'-diethylamidinourea
1-(2,6-dichloro-3,5-dimethoxyphenyl)-3-N,N'-diethylamidinourea
1-(2,6-dichloro-3,4-methylenedioxyphenyl)-3-N,N'-diethylamidinourea
1-(2-chloro-6-methyl-3-methoxyphenyl)-3-N,N'-diethylamidinourea
1-(2-chloro-6-methyl-4-benzyloxyphenyl)-3-N,N'-diethylamidinourea
1-(2-chloro-6-methyl-5-benzyloxyphenyl)-3-N,N'-diethylamidinourea
1-(2-chloro-6-methyl-3,4-diacetoxyphenyl)-3-N,N'-diethylamidinourea
1-(2-chloro-6-methyl-3,5-dibenzyloxyphenyl)-3-N,N'-diethylamidinourea
1-(2-chloro-6-methyl-3,4-dimethoxyphenyl)-3-N,N'-diethylamidinourea
1-(2-chloro-6-methyl-3,4,5-triacetoxyphenyl)-3-N,N'-diethylamidinourea
1-(2,6-diethyl-4-acetoxyphenyl)-3-N,N'-diethylamidinourea
1-(2,6-diethyl-3-methoxy-4-hydroxyphenyl)-3-N,N'-diethylamidinourea
1-(2,6-diethyl-3,5-dibenzyloxyphenyl)-3-N,N'-diethylamidinourea
1-(2,6-diethyl-3,4,5-triacetoxyphenyl)-3-N,N'-diethylamidinourea
1-(2,6-diethyl-3-ethoxyphenyl)-3-N,N'-diethylamidinourea 1-(2,6-dimethyl-4-ethoxyphenyl)-1-methyl-3-n-propylamidinourea
1-(2,6-dimethyl-3-methoxyphenyl)-1-methyl-3-n-propylamidinourea
1-(2,6-dimethyl-3,4-dimethoxyphenyl)-1-methyl-3-n-propylamidinourea
1-(2,6-dimethyl-3-hydroxy-5-methoxyphenyl)-1-methyl-3-n-propylamidinourea
1-(2,6-dimethyl-3,4,5-trimethoxyphenyl)-1-methyl-3-n-propylamidinourea
1-(2,6-dichloro-4-benzyloxyphenyl)-1-methyl-3-n-propylamidinourea
1-(2,6-dichloro-3-methoxyphenyl)-1-methyl-3-n-propylamidinourea
1-(2,6-dichloro-3-methoxy-4-hydroxyphenyl)-1-methyl-3-n-propylamidinourea 1-(2,6-dichloro-3,5-dimethoxyphenyl)-1-methyl-3-n-propylamidinourea
1-(2,6-dichloro-3,4-methylenedioxyphenyl)-1-methyl-3-n-propylamidinourea
1-(2-chloro-6-methyl-3-methoxyphenyl)-1-methyl-3-n-propylamidinourea
1-(2-chloro-6-methyl-4-benzyloxyphenyl)-1-methyl-3-n-propylamidinourea
1-(2-chloro-6-methyl-5-benzyloxyphenyl)-1-methyl-3-n-propylamidinourea
1-(2-chloro-6-methyl-3,4-diacetoxyphenyl)-1-methyl-3-n-propylamidinourea
1-(2-chloro-6-methyl-3,5-dibenzyloxyphenyl-1-methyl-3-n-propylamidinourea
1-(2-chloro-6-methyl-3,4-dimethoxyphenyl)-1-methyl-3-n-propylamidinourea
1-(2-chloro-6-methyl-3,4,5-triacetoxyphenyl)-1-methyl-3-n-propylamidinourea
1-(2,6-diethyl-4-acetoxyphenyl)-1-methyl-3-n-propylamidinourea
1-(2,6-diethyl-3-methoxy-4-hydroxyphenyl)-1-methyl-3-n-propylamidinourea
1-(2,6-diethyl-3,5-dibenzyloxyphenyl)-1-methyl-3-n-propylamidinourea
1-(2,6-diethyl-3,4,5-triacetoxyphenyl)-1-methyl-3-n-propylamidinourea
1-(2,6-diethyl-3-ethoxyphenyl)-1-methyl-3-n-propylamidinourea 1-(2,6-dimethyl-4-acetoxyphenyl)-3-methylamidinourea
1-(2,6-dimethyl-4-methoxyphenyl)-3-methylamidinourea
1-(2,6-dimethyl-4-ethoxyphenyl)-3-methylamidinourea
1-(2,6-dimethyl-4-n-propoxyphenyl)-3-methylamidinourea
1-(2,6-dimethyl-4-benzyloxyphenyl)-3-methylamidinourea 1-(2,6-dimethyl-4-trifluoromethoxyphenyl)-3-methylamidinourea
1-(2,6-dimethyl-4-trifluoroacetoxyphenyl)-3-methylamidinourea 1-(2,6-dichloro-4-acetoxyphenyl)-3-methylamidinourea
1-(2,6-dichloro-4-methoxyphenyl)-3-methylamidinourea
1-(2,6-dichloro-4-ethoxyphenyl)-3-methylamidinourea
1-(2,6-dichloro-4-n-propoxyphenyl)-3-methylamidinourea
1-(2,6-dichloro-4-benzyloxyphenyl)-3-methylamidinourea 1-(2,6-dichloro-4-trifluoromethoxyphenyl)-3-methylamidinourea
1-(2,6-dichloro-4-trifluoroacetoxyphenyl)-3-methylamidinourea 1-(2,6-diethyl-4-acetoxyphenyl)-3-methylamidinourea
1-(2,6-diethyl-4-methoxyphenyl)-3-methylamidinourea
1-(2,6-diethyl-4-ethoxyphenyl)-3-methhylamidinourea
1-(2,6-diethyl-4-n-propoxyphenyl)-3-methylamidinourea
1-(2,6-diethyl-4-benzyloxyphenyl)-3-methylamidinourea 1-(2,6-diethyl-4-trifluoromethoxyphenyl)-3-methylamidinourea
1-(2,6-diethyl-4-trifluoroacetoxyphenyl)-3-methylamidinourea 1-(2,6-dimethyl-4-acetoxyphenyl)-3-ethylamidinourea
1-(2,6-dimethyl-4-methoxyphenyl)-3-ethylamidinourea
1-(2,6-dimethyl-4-ethoxyphenyl)-3-ethylamidinourea
1-(2,6-dimethyl-4-n-propoxyphenyl)-3-ethylamidinourea
1-(2,6-dimethyl-4-benzyloxyphenyl)-3-ethylamidinourea
1-(2,6-dimethyl-4-trifluoromethoxyphenyl)-3-ethylamidinourea
1-(2,6-dimethyl-4-trifluoroacetoxyphenyl)-3-ethylamidinourea
1-(2,6-dimethyl-4-hydroxyphenyl)-3-n-propylamidinourea
1-(2,6-dimethyl-4-acetoxyphenyl)-3-n-propylamidinourea
1-(2,6-dimethyl-4-methoxyphenyl)-3-n-propylamidinourea
1-(2,6-dimethyl-4-ethoxyphenyl)-3-n-propylamidinourea
1-(2,6-dimethyl-4-n-propoxyphenyl)-3-n-propylamidinourea
1-(2,6-dimethyl-4-benzyloxyphenyl)-3-n-propylamidinourea 1-(2,6-dimethyl-4-trifluoromethoxyphenyl)-3-n-propylamidinourea
1-(2,6-dimethyl-4-trifluoroacetoxyphenyl)-3-n-propylamidinourea
1-(2,6-dimethyl-3-hydroxyphenyl)-3-methylamidinourea
1-(2,6-dimethyl-3-acetoxyphenyl)-3-n-methylamidinourea
1-(2,6-dimethyl-3-methoxyphenyl)-3-methylamidinourea
1-(2,6-dimethyl-3-ethoxyphenyl)-3-methylamidinourea
1-(2,6-dimethyl-3-n-propoxyphenyl)-3-methylamidinourea
1-(2,6-dimethyl-3-benzyloxyphenyl)-3-methylamidinourea 1-(2,6-dimethyl-3-trifluoromethoxyphenyl)-3-methylamidinourea
1-(2,6-dimethyl-3-trifluoroacetoxyphenyl)-3-methylamidinourea
1-(2,6-dichloro-3-hydroxyphenyl)-3-ethylamidinourea
1-(2,6-dichloro-3-acetoxyphenyl)-3-methylamidinourea
1-(2,6-dichloro-3-methoxyphenyl)-3-methylamidinourea
1-(2,6-dichloro-3-ethoxyphenyl)-3-methylamidinourea
1-(2,6-dichloro-3-n-propoxyphenyl)-3-methylamidinourea
1-(2,6-dichloro-3-benzyloxyphenyl)-3-methylamidinourea 1-(2,6-dichloro-3-trifluoromethoxyphenyl)-3-methylamidinourea
1-(2,6-dichloro-3-trifluoroacetoxyphenyl)-3-methylamidinourea
1-(2,6-diethyl-3-hydroxyphenyl)-3-methylamidinourea
1-(2,6-diethyl-3-acetoxyphenyl)-3-methylamidinourea
1-(2,6-diethyl-3-methoxyphenyl)-3-methylamidinourea
1-(2,6-diethyl-3-ethoxyphenyl)-3-methylamidinourea
1-(2,6-diethyl-3-n-propoxyphenyl)-3-methylamidinourea 1-(2,6-diethyl-3-benzyloxyphenyl)-3-methylamidinourea 1-(2,6-diethyl-3-trifluoromethoxyphenyl)-3-methylamidinourea 1-(2,6-diethyl-3-trifluoroacetoxyphenyl)-3-methylamidinourea 1-(2,6-dimethyl-3-hydroxyphenyl)-3-ethylamidinourea 1-(2,6-dimethyl-3-acetoxyphenyl)-3-ethylamidinourea 1-(2,6-dimethyl-3-methoxyphenyl)-3-ethylamidinourea 1-(2,6-dimethyl-3-ethoxyphenyl)-3-ethylamidinourea 1-(2,6-dimethyl-3-n-propoxyphenyl)-3-ethylamidinourea 1-(2,6-dimethyl-3-benzyloxyphenyl)-3-ethylamidinourea 1-(2,6-dimethyl-3-trifluoromethoxyphenyl)-3-ethylamidinourea 1-(2,6-dimethyl-3-trifluoroacetoxyphenyl)-3-ethylamidinourea 1-(2,6-dimethyl-3-hydroxyphenyl)-3-n-propylamidinourea 1-(2,6-dimethyl-3-acetoxyphenyl)-3-n-propylamidinourea 1-(2,6-dimethyl-3-methoxyphenyl)-3-n-propylamidinourea 1-(2,6-dimethyl-3-ethoxyphenyl)-3-n-propylamidinourea 1-(2,6-dimethyl-3-n-propoxyphenyl)-3-n-propylamidinourea 1-(2,6-dimethyl-3-benzyloxyphenyl)-3-n-propylamidinourea 1-(2,6-dimethyl-3-trifluoromethoxyphenyl)-3-n-propylamidinourea 1-(2,6-dimethyl-3-trifluoroacetoxyphenyl)-3-n-propylamidinourea 1-(2,6-dimethyl-3,4-dihydroxyphenyl)-3-methylamidinourea 1-(2,6-dimethyl-3,4-diacetoxyphenyl)-3-methylamidinourea 1-(2,6-dimethyl-3,4-dimethoxyphenyl)-3-methylamidinourea 1-(2,6-dimethyl-3,4-diethoxyphenyl)-3-methylamidinourea 1-(2,6-dimethyl-3,4-dibenzyloxyphenyl)-3-methylamidinourea 1-(2,6-dimethyl-3,4-ditrifluoromethoxyphenyl)-3-methylamidinourea 1-(2,6-dimethyl-3,4-ditrifluoroacetoxyphenyl)-3-methylamidinourea 1-(2,6-dichloro-3,4-dihydroxyphenyl)-3-methylamidinourea 1-(2,6-dichloro-3,4-diacetoxyphenyl)-3-methylamidinourea 1-(2,6-dichloro-3,4-dimethoxyphenyl)-3-methylamidinourea 1-(2,6-dichloro-3,4-diethoxyphenyl)-3-methylamidinourea 1-(2,6-dichloro-3,4-dibenzyloxyphenyl)-3-methylamidinourea 1-(2,6-dichloro-3,4-ditrifluoromethoxyphenyl)-3-methylamidinourea 1-(2,6-dichloro-3,4-ditrifluoroacetoxyphenyl)-3-methylamidinourea 1-(2,6-diethyl-3,4-dihydroxyphenyl)-3-methylamidinourea 1-(2,6-diethyl-3,4-diacetoxyphenyl)-3-methylamidinourea 1-(2,6-diethyl-3,4-dimethoxyphenyl)-3-methylamidinourea 1-(2,6-diethyl-3,4-diethoxyphenyl)-3-methylamidinourea 1-(2,6-diethyl-3,4-dibenzyloxyphenyl)-3-methylamidinourea 1-(2,6-diethyl-3,4-ditrifluoromethoxyphenyl)-3-methylamidinourea 1-(2,6-diethyl-3,4-ditrifluoroacetoxyphenyl)-3-methylamidinourea 1-(2,6-dimethyl-3,4-dihydroxyphenyl)-3-ethylamidinourea 1-(2,6-dimethyl-3,4-diacetoxyphenyl)-3-ethylamidinourea 1-(2,6-dimethyl-3,4-dimethoxyphenyl)-3-ethylamidinourea 1-(2,6-dimethyl-3,4-diethoxyphenyl)-3-ethylamidinourea 1-(2,6-dimethyl-3,4-dibenzyloxyphenyl)-3-ethylamidinourea 1-(2,6-dimethyl-3,4-ditrifluoromethoxyphenyl)-3-ethylamidinourea 1-(2,6-dimethyl-3,4-ditrifluoroacetoxyphenyl)-3-ethylamidinourea 1-(2,6-dimethyl-3,4-dihydroxyphenyl)-3-n-propylamidinourea 1-(2,6-dimethyl-3,4-diacetoxyphenyl)-3-n-propylamidinourea 1-(2,6-dimethyl-3,4-dimethoxyphenyl)-3-n-propylamidinourea 1-(2,6-dimethyl-3,4-diethoxyphenyl)-3-n-propylamidinourea 1-(2,6-dimethyl-3,4-dibenzyloxyphenyl)-3-n-propylamidinourea 1-(2,6-dimethyl-3,4-ditrifluoromethoxyphenyl)-3-n-propylamidinourea 1-(2,6-dimethyl-3,4-ditrifluoroacetoxyphenyl)-3-n-propylamidinourea 1-(2,6-dimethyl-3,5-dihydroxyphenyl)-3-methylamidinourea 1-(2,6-dimethyl-3,5-diacetoxyphenyl)-3-methylamidinourea 1-(2,6-dimethyl-3,5-dimethoxyphenyl)-3-methylamidinourea 1-(2,6-dimethyl-3,5-diethoxyphenyl)-3-methylamidinourea 1-(2,6-dimethyl-3,5-dibenzyloxyphenyl)-3-methylamidinourea 1-(2,6-dimethyl-3,5-diphenoxyphenyl)-3-methylamidinourea 1-(2,6-dimethyl-3,5-ditrifluoromethoxyphenyl)-3-methylamidinourea 1-(2,6-dimethyl-3,5-ditrifluoroacetoxyphenyl)-3-methylamidinourea 1-(2,6-dichloro-3,5-dihydroxyphenyl)-3-methylamidinourea 1-(2,6-dichloro-3,5-diacetoxyphenyl)-3-methylamidinourea 1-(2,6-dichloro-3,5-diethoxyphenyl)-3-methylamidinourea 1-(2,6-dichloro-3,5-dibenzyloxyphenyl)-3-methylamidinourea 1-(2,6-dichloro-3,5-ditrifluoromethoxyphenyl)-3-methylamidinourea 1-(2,6-dichloro-3,5-ditrifluoroacetoxyphenyl)-3-methylamidinourea 1-(2,6-diethyl-3,5-dihydroxyphenyl)-3-methylamidinourea 1-(2,6-diethyl-3,5-diacetoxyphenyl)-3-methylamidinourea 1-(2,6-diethyl-3,5-dimethoxyphenyl)-3-methylamidinourea 1-(2,6-diethyl-3,5-diethoxyphenyl)-3-methyylamidinourea 1-(2,6-diethyl-3,5-dibenzyloxyphenyl)-3-methylamidinourea 1-(2,6-diethyl-3,5-ditrifluoromethoxyphenyl)-3-methylamidinourea 1-(2,6-diethyl-3,5-ditrifluoroacetoxyphenyl)-3-methylamidinourea 1-(2,6-dimethyl-3,5-dihydroxyphenyl)-3-ethylamidinourea 1-(2,6-dimethyl-3,5-diacetoxyphenyl)-3-ethylamidinourea 1-(2,6-dimethyl-3,5-dimethoxyphenyl)-3-ethylamidinourea 1-(2,6-dimethyl-3,5-diethoxyphenyl)-3-ethylamidinourea 1-(2,6-dimethyl-3,5-dibenzyloxyphenyl)-3-ethylamidinourea 1-(2,6-dimethyl-3,5-ditrifluoromethoxyphenyl)-3-ethylamidinourea 1-(2,6-dimethyl-3,5-ditrifluoroacetoxyphenyl)-3-ethylamidinourea 1-(2,6-dimethyl-3,5-dihydroxyphenyl)-3-n-propylamidinourea 1-(2,6-dimethyl-3,5-diacetoxyphenyl)-3-n-propylamidinourea 1-(2,6-dimethyl-3,5-dimethoxyphenyl)-3-n-propylamidinourea 1-(2,6-dimethyl-3,5-diethoxyphenyl)-3-n-propylamidinourea 1-(2,6-dimethyl-3,5-dibenzyloxyphenyl)-3-n-propylamidinourea 1-(2,6-dimethyl-3,5-ditrifluoromethoxyphenyl)-3-n-propylamidinourea 1-(2,6-dimethyl-3,5-ditrifluoroacetoxyphenyl)-3-n-propylamidinourea 1-(2,6-dimethyl-3,4,5-triacetoxyphenyl)-3-methylamidinourea 1-(2,6-dimethyl-3,4,5-trimethoxyphenyl)-3-methylamidinourea 1-(2,6-dimethyl-3,4,5-triethoxyphenyl)-3-methylamidinourea 1-(2,6-dichloro-3,4,5-trihydroxyphenyl)-3-methylamidinourea 1-(2,6-dichloro-3,4,5-triacetoxyphenyl)-3-methylamidinourea 1-(2,6-dichloro-3,4,5-trimethoxyphenyl)-3-methylamidinourea 1-(2,6-dichloro-3,4,5-triethoxyphenyl)-3-methylamidinourea 1-(2,6-diethyl-3,4,5-triacetoxyphenyl)-3-methylamidinourea 1-(2,6-diethyl-3,4,5-trimethoxyphenyl)-3-methylamidinourea 1-(2,6-diethyl-3,4,5-triethoxyphenyl)-3-methylamidinourea 1-(2,6-dimethyl-3,4,5-trihydroxyphenyl)-3-ethylamidinourea 1-(2,6-dimethyl-3,4,5-triacetoxyphenyl)-3-ethylamidinourea 1-(2,6-dimethyl-3,4,5-trimethoxyphenyl)-3-ethylamidinourea 1-(2,6-dimethyl-3,4,5-triethoxyphenyl)-3-ethylamidinourea 1-(2,6-dimethyl-3,4,5-triacetoxyphenyl)-3-n-propylamidinourea 1-(2,6-dimethyl-3,4,5-trimethoxyphenyl)-3-n-propylamidinourea 1-(2,6-dimethyl-3,4,5-triethoxyphenyl)-3-n-propylamidinourea

We claim:

1. A method for lowering blood pressure in mammalian species comprising administering orally to a patient an orally effective amount of an amidinourea compound of the formula $$\begin{array}{c} R_3 \quad R_2 \\ R_4 - \bigcirc - N - C - N = C \diagup N \diagdown R' \\ | \quad \| \quad \diagdown N \diagup R'' \\ R_5 \quad R_6 \quad R_1 \quad \diagdown R''' \end{array}$$

where:
R, R', R'', R''' and $R_1$ may be the same or different and and are hydrogen or lower alkyl, provided that at least one of R, R', R'' and R''' is other than hydrogen;

$R_2$ and $R_6$ may be the same or different and are lower alkyl, halo, lower alkoxy, halo lower alkyl, nitro, or lower alkylsulfonyl;

$R_4$ is hydroxy;

$R_3$ and $R_5$ may be the same or different and are hydrogen, hydroxy, lower alkoxy, arloweralkoxy, lower alkynyloxy, lower alkenyloxy, halo loweralkyl acyloxy or loweralkyl acyloxy;

provided that $R_3$, $R_4$ and $R_5$ are not all hydroxy; and wherein:

arloweralkoxy means lower alkoxy substituted with phenyl or phenyl in which one or more of the phenyl hydrogens has been replaced by the same or different substituents selected from the group consisting of halo, lower alkyl, halolower alkyl, nitro, amino, lower alkanoyl, hydroxy, lower hydroxy, phenyl-lower alkoxy, lower alkanoyl, cyano, halo-lower alkoxy, and lower alkyl sulfonyl;

or a nontoxic pharmaceutically acceptable salt thereof.

2. A method according to claim 1, wherein R and $R_1$ are hydrogen and at least one of R', R'' and R''' is lower alkyl.

3. A method according to claim 2, wherein $R_2$ and $R_6$ may be the same or different and are lower alkyl, halo or lower alkoxy.

4. A method for lowering blood pressure in mammalian species comprising administering orally to a patient an orally effective amount of 1-(2,6-dimethyl-4-hydroxyphenyl)-3-N-methyl amidinourea or a pharmaceutically acceptable salt thereof.

* * * * *